US00PP17467P2

(12) United States Plant Patent
Ghyselen

(10) Patent No.: US PP17,467 P2
(45) Date of Patent: Mar. 6, 2007

(54) ***PERSICARIA* PLANT NAMED 'FAT DOMINO'**

(50) Latin Name: *Persicaria amplexicaulis*
Varietal Denomination: Fat Domino

(75) Inventor: Chris Ghyselen, Oedelem (BE)

(73) Assignee: Future Plants Licentie B.V., Lisserbroek (NL)

( * ) Notice: Subject to any disclaimer, the term of this patent is extended or adjusted under 35 U.S.C. 154(b) by 35 days.

(21) Appl. No.: 11/151,835

(22) Filed: Jun. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Persicaria* plant named 'Fat Domino', characterized by its upright and outwardly spreading plant habit; dark red purple-colored flowers on long racemes; freely and continuous flowering habit; and good garden performance.

2 Drawing Sheets

Botanical designation: *Persicaria amplexicaulis.*
Cultivar denomination: 'Fat Domino'.

BACKGROUND OF THE INVENTION

The present Invention relates to a new and distinct cultivar of *Persicaria* plant, botanically known as *Persicaria amplexicaulis,* and hereinafter referred to by the cultivar name Fat Domino.

The new *Persicaria* is a product of a planned breeding program conducted by the Inventor in Oedelem (Beernem), Belgium. The objective of the breeding program was to create new *Persicaria* cultivars with attractive flower coloration.

The new *Persicaria* originated from a cross-pollination made by the Inventor in 2001 in Oedelem (Beernem), Belgium of an unnamed selection of *Persicaria amplexicaulis,* not patented, as the female, or seed, parent with an unnamed selection of *Persicaria amplexicaulis,* not patented, as the male, or pollen, parent. The new *Persicaria* was discovered and selected by the Inventor as a flowering plant within the progeny of the stated cross-pollination in a controlled environment in Oedelem (Beernem), Belgium during the summer of 2002.

Asexual reproduction of the new cultivar by cuttings at Oedelem (Beernem), Belgium since 2002, has shown that the unique features of this new *Persicaria* are stable and reproduced true to type in successive generations.

SUMMARY OF THE INVENTION

Plants of the cultivar Fat Domino have not been observed under all possible environmental conditions. The phenotype may vary somewhat with variations in environment such as temperature and light level without, however, any variance in genotype.

The following traits have been repeatedly observed and are determined to be the unique characteristics of 'Fat Domino'. These characteristics in combination distinguish 'Fat Domino' as a new and distinct cultivar of *Persicaria:*

1. Upright and outwardly spreading plant habit.
2. Dark red purple-colored flowers on long racemes.
3. Freely and continuous flowering habit.
4. Good garden performance.

Plants of the new *Persicaria* differ primarily from plants of the parent selections in flower color as plants of the parent selections have lighter red-colored flowers. In addition, plants of the new *Persicaria* have larger inflorescences than plants of the female parent selection and a stronger, more upright plant habit than plants of the male parent selection.

Plants of the new *Persicaria* can be compared to the *Persicaria amplexicaulis* cultivar Taurus, disclosed in U.S. Plant Pat. No. 9,682. Plants of the new differ from plants of the cultivar Taurus in the following characteristics:

1. Plants of the new *Persicaria* have darker green-colored leaves than plants of the cultivar Taurus.
2. Plants of the new *Persicaria* have longer racemes than plants of the cultivar Taurus.
3. Plants of the new *Persicaria* have darker-colored flowers than plants of the cultivar Taurus.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Persicaria.*

The photograph on the first sheet comprises a side perspective view of a typical flowering plant of 'Fat Domino'.

The photograph at the top of the second sheet is a close-up view of a typical inflorescence of 'Fat Domino'.

The photograph at the bottom of the second sheet is a close-up view of the upper surface of a typical leaf of 'Fat Domino'.

DETAILED BOTANICAL DESCRIPTION

The aforementioned photographs, following observations and measurements describe plants grown in Lisserbroek, The Netherlands, in an outdoor nursery and under commercial production practices during the summer and fall. Plants were about two years old when the photographs and description were taken. During the production of the plants, day temperatures ranged from 12 to 24° C. and night temperatures ranged from 4 to 12° C. In the following description, color references are made to The Royal Horticultural Society Colour Chart, 2001 Edition, except where general terms of ordinary dictionary significance are used.

Botanical classification: *Persicaria amplexicaulis* cultivar Fat Domino.

Parentage:

*Female parent.*—Unnamed selection of *Persicaria amplexicaulis,* not patented.

*Male parent.*—Unnamed selection of *Persicaria amplexicaulis,* not patented.

Propagation:

*Type.*—By cuttings.

*Time to initiate roots.*—About 30 days at 20° C.

*Time to produce a rooted plant.*—About 50 days at 20° C.

*Root description.*—Fibrous; moderately fine; very dark brown to almost black in color.

*Rooting habit.*—Freely branching; dense.

Plant description:

*Plant form/habit.*—Upright and outwardly spreading; broad inverted triangle; moderately vigorous growth habit.

*Plant height.*—About 82 cm.

*Plant width* (*spread*).—About 72 cm.

*Lateral branches.*—Length: About 39.1 cm. Diameter: About 4 mm. Internode length: About 14.1 cm. Strength: Strong. Texture: Smooth, glabrous. Color: 144A.

*Foliage description.*—Arrangement: Alternate, simple. Length: About 15.3 cm. Width: About 7.2 cm. Shape: Ovate. Apex: Apiculate. Base: Cordate. Margin: Finely and irregularly serrate; undulate. Texture, upper and lower surfaces: Pubescent, scabrous. Venation pattern: Pinnate. Color: Developing leaves, upper surface: 137A. Developing leaves, upper and lower surfaces: N138B. Fully expanded leaves, upper surface: Between 137A and 147A. Fully expanded leaves, lower surface: 147B. Venation, upper surface: 151A. Venation, lower surface: 145A to 145B. Petiole length: About 1.6 cm. Petiole diameter: About 4 mm. Petiole color: 144B.

Flower description:

*Flower type/habit.*—Single rotate flowers arranged in terminal racemes; flowers face outward to slightly upright. Freely flowering habit with about 165 flower buds and flowers per inflorescence.

*Fragrance.*—Faint.

*Natural flowering season.*—Continuously flowering from late August through October in The Netherlands. Flowers not persistent.

*Postproduction longevity.*—Flowers last about one week on the plant.

*Inflorescence height.*—About 10 cm.

*Inflorescence diameter.*—About 2.5 cm.

*Flower buds.*—Height: About 5 mm. Diameter: About 2.5 mm. Shape: Ovate. Color: 53A to 53B.

*Flowers.*—Diameter: About 9 mm. Depth: About 7 mm.

*Petals.*—Quantity per flower: Typically five in a single whorl. Length: About 5 mm. Lobe width: About 2 mm. Shape: Ovate. Apex: Bluntly acute to obtuse. Margin: Entire. Texture, upper and lower surfaces: Smooth, glabrous. Color: Developing petals, upper and lower surfaces: 59C. Fully opened petals, upper surface: 59C; towards the base, 59D; color becoming closer to 59B with development. Fully opened petals, lower surface: 59C.

*Sepals.*—Sepals have not been observed.

*Peduncles.*—Length: About 29.1 cm. Diameter: About 2.5 mm. Aspect: About 10° from vertical. Strength: Strong. Color: 144A.

*Pedicels.*—Length: About 5 mm. Diameter: About 0.5 mm. Aspect: About 30° from vertical. Strength: Moderately strong. Color: 59C.

*Reproductive organs.*—Stamens: Quantity per flower: Typically six. Filament length: About 4 mm. Filament color: 59C; towards the base, 59D. Anther shape: Elliptic. Anther length: About 0.5 mm. Anther color: 202A. Pollen amount: Scarce. Pollen color: 202D. Pistils: Quantity per flower: Typically three. Pistil length: About 4 mm. Stigma shape: Acute. Stigma color: 60A. Style length: About 3.8 mm. Style color: 60B. Ovary color: 144B.

*Seed/fruit.*—Seed and fruit development have not been observed.

Disease/pest resistance: Plants of the new *Persicaria* have not been noted to be resistant to pathogens and pests common to *Persicaria.*

Garden performance: Plants of the new *Persicaria* have been observed to have good garden performance and tolerate rain, wind, are hardy to USDA Zone 5 and tolerate temperatures as high as 35° C.

It is claimed:

1. A new and distinct cultivar of *Persicaria* plant named 'Fat Domino', as illustrated and described.

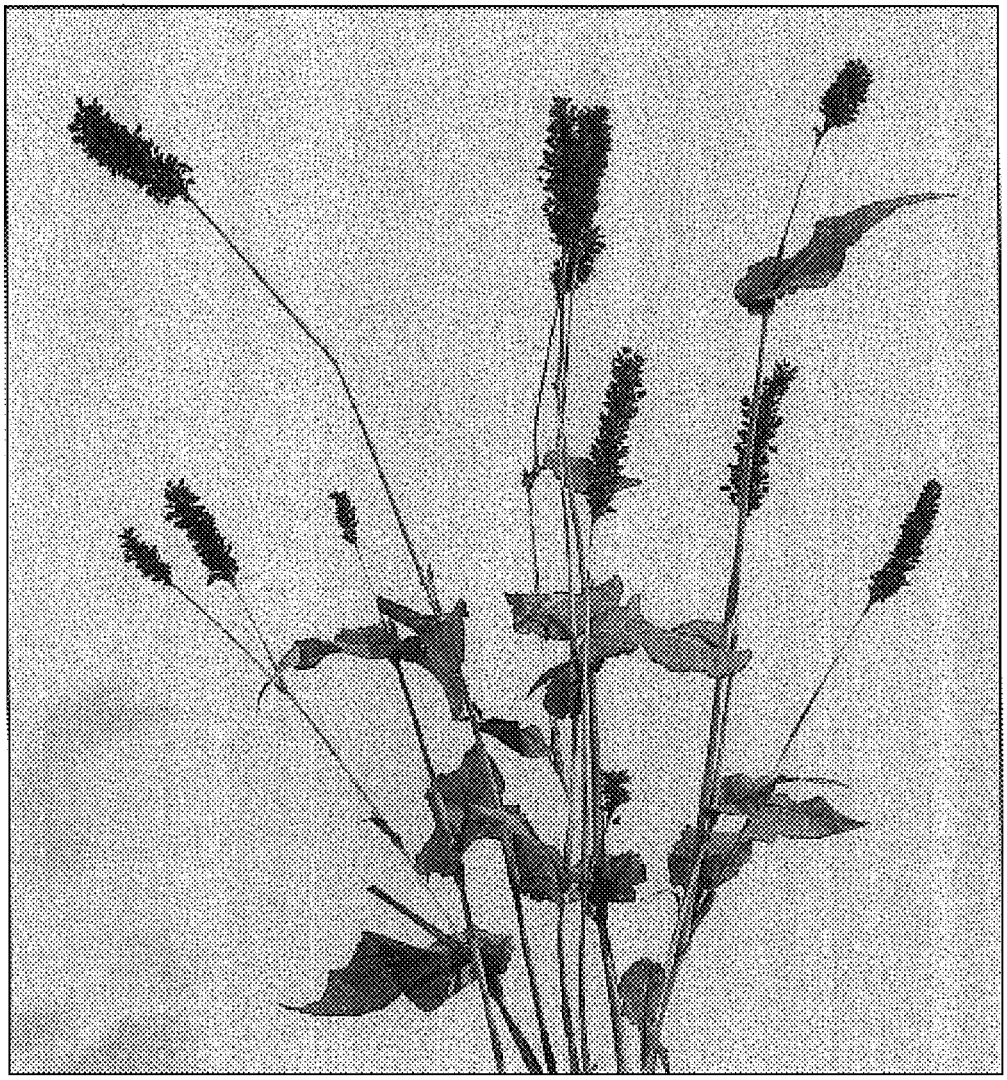

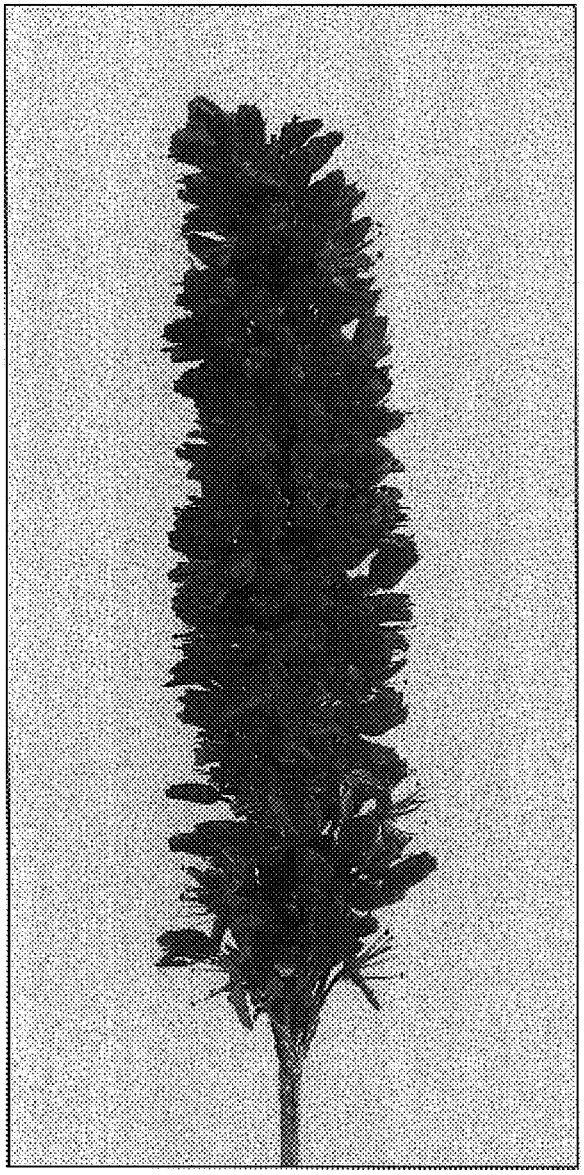
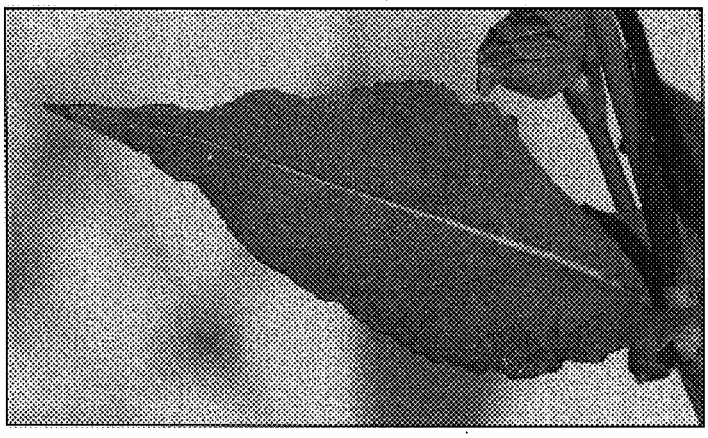

* * * * *